Figure 1:
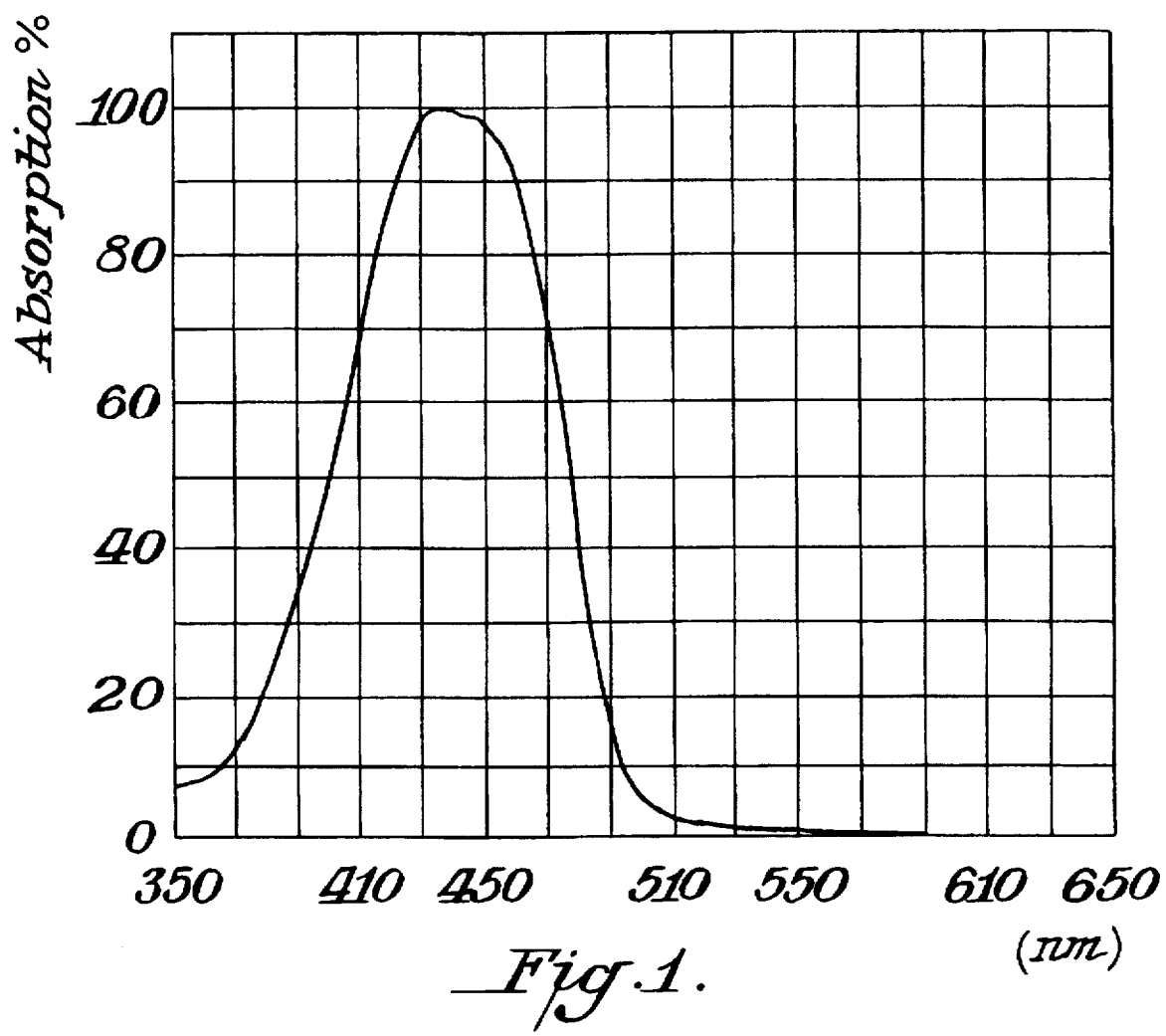

United States Patent [19]

Öhlschläger et al.

[11] Patent Number: 5,776,667
[45] Date of Patent: Jul. 7, 1998

[54] COLOR PHOTOGRAPHIC RECORDING MATERIAL HAVING A YELLOW FILTER LAYER WHICH CONTAINS AN ARYLIDENE DYE OF ISOXAZOLONE AS THE YELLOW FILTER DYE

[75] Inventors: Hans Öhlschläger, Bergisch Gladbach; Hans Langen, Bonn; Klaus Sinzger, Leverkusen, all of Germany

[73] Assignee: AGFA AG, Germany

[21] Appl. No.: 779,915

[22] Filed: Jan. 7, 1997

[30] Foreign Application Priority Data

Jan. 12, 1996 [DE] Germany .......................... 196 00 903.0
Nov. 11, 1996 [DE] Germany .......................... 196 46 402.1

[51] Int. Cl.⁶ ...................................................... G03C 1/83
[52] U.S. Cl. ................................................ 430/517; 430/507
[58] Field of Search ...................................... 430/507, 517

[56] References Cited

U.S. PATENT DOCUMENTS

| 5,264,333 | 11/1993 | Yamanouchi et al. | 430/517 |
| 5,328,818 | 7/1994 | Fukuzawa et al. | 430/507 |
| 5,594,047 | 1/1997 | Nielsen et al. | 430/517 |

FOREIGN PATENT DOCUMENTS

| 412 379 | 7/1990 | European Pat. Off. . |
| 412379 | 2/1991 | European Pat. Off. . |
| 44 28 292 | 2/1996 | Germany . |

*Primary Examiner*—Hoa Van Le
*Attorney, Agent, or Firm*—Connolly & Hutz

[57] ABSTRACT

A color photographic recording material comprises in a yellow filter layer at least one dye of one of the formulae I and II

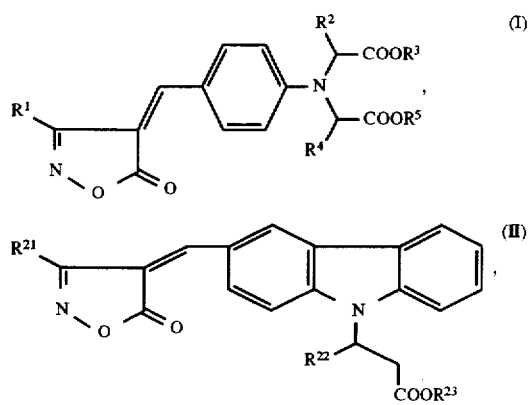

in which
$R^1$, $R^3$ and $R^5$ (mutually independently) mean alkyl, cycloalkyl or aryl;
$R^2$ and $R^4$ (mutually independently) mean hydrogen or alkyl;
$R^{21}$ means a residue as $R^1$;
$R^{22}$ means a residue as $R^2$;
$R^{23}$ means a residue as $R^1$;
provided that in formula I none of the residues $R^1$ to $R^5$ contains an alkyl chain of more than 3 carbon atoms.

The dyes exhibit suitable absorption as yellow filter dyes and are completely decolored during processing.

20 Claims, 2 Drawing Sheets

COLOR PHOTOGRAPHIC RECORDING MATERIAL HAVING A YELLOW FILTER LAYER WHICH CONTAINS AN ARYLIDENE DYE OF ISOXAZOLONE AS THE YELLOW FILTER DYE

This invention relates to a colour photographic recording material having at least one silver halide emulsion layer and a yellow filter layer, which comprises an arylidene dye of isoxazolone as the yellow filter dye.

It is known to incorporate light-absorbing dyes into photographic materials. Such a dye may be used, for example, in a non-photosensitive layer which is arranged above a photosensitive silver halide emulsion layer or between two photosensitive emulsion layers in order to protect the underlying emulsion layers from the action of the light of the wavelength absorbed by the dye. It is also known to use dyes as acutance dyes in a photosensitive emulsion layer itself or as anti-halation dyes in a layer known as an anti-halation layer.

If it is necessary to control or regulate the spectral composition of the incident light falling on a photosensitive photographic silver halide emulsion layer, a coloured layer may be introduced for this purpose into the photosensitive photographic recording material, which layer is then known as a filter layer. Thus, for example, in colour photographic materials a yellow dyed filter layer is usually arranged between the blue-sensitive layer and the underlying green-sensitive and red-sensitive layers in order to keep the blue light away from the green- and red-sensitive layers.

High requirements are placed upon the dyes used in photographic materials. They must not only exhibit spectral absorption suitable for their intended purpose, but should also be photochemically inert. In particular, the dyes must have no disadvantageous effects on the quality of the photographic silver halide emulsion; they must accordingly not, for example, reduce sensitivity or cause fogging. Moreover, while the dyes should indeed be non-diffusible within the material, they must be completely and irreversibly decoloured or washed out of the layer during processing of the material so that no unwanted coloration remains on the exposed and developed photographic material.

These requirements are not satisfactorily fulfilled by known dyes. The colloidal silver conventionally used in yellow filter layers readily results in fogging, in adjacent emulsion layers. Water-soluble organic dyes, which are rendered non-diffusible by the incorporation of long alkyl chains, as are mentioned in DE 2 259 746, are not decoloured or only incompletely so in ordinary photographic processing baths. When dyes are immobilised with a mordant, for example GB 1 034 044, U.S. Pat. No. 3,740,228 or DE-A-2 941 819, the mordant effect is not generally sufficient to immobilise the dye to the required extent in the mordant layer.

Certain sulphonamide-substituted azo dyes are already known from DE-A-2 347 590 and the corresponding printed patent specification DL 107 990 and DE-A-4 428 292, which are apparently suitable in particular for yellow filter layers. However, these dyes too prove inadequate with regard to non-diffusibility; they are not decoloured and thus accumulate in the developer. These dyes moreover in general readily crystallise out of gelatine solution which results in casting defects during subsequent processing. Reference is made in this connection to published patent specification DL 130 265, where it is also stated that the azo dyes known from DL-PS 107 990 have a tendency towards unwanted crystallisation and cause unacceptably marked residual coloration.

Arylidene dyes prepared from cyanoacetic acid esters and aldehydes have already been used. These dyes may readily be incorporated into the layer and exhibit usable absorption. However, the dyes are not washed out of the layer and are also not decoloured in the layer.

EP-A-0 401 709 claims arylidene dyes of isoxazolone as a filter dye for X-ray materials, but there is no indication that such dyes may also be used in colour materials. Similar dyes are also described in EP-A-0 412 379 as correction dyes in colour materials. As such, as is clear from the examples in the patent, they are used together with black colloidal silver in an anti-halo layer beneath the photosensitive layers. As correction dyes, the dyes must not be decoloured on processing in photographic baths, which is achieved in the compounds of EP-A-0 412 379 by introducing a fat residue. In contrast to correction dyes, yellow filter dyes should be decoloured as completely as possible in photographic baths. Use of the above-stated dyes as yellow filter dyes is also contraindicated by their long-wave absorption. Dyes prepared from dialkylaminobenzaldehydes and 3-arylisoxazolones absorb at such long wavelengths that, when used as yellow filter dyes, a considerable proportion of the green sensitivity of the underlying layer is cut off. Substitution on the phenyl ring of the aldehyde moiety shifts absorption to still longer wavelengths.

The object of the invention is to provide dyes which may be used in yellow filter layers of colour photographic recording materials. These dyes should not exhibit the above-stated disadvantages and should in particular satisfy the requirements of photographic applications with regard to non-diffusibility, decolorability and absorption characteristics.

Now, there have been found condensation products of 3-alkylisoxazolones with p-N,N-biscarbalkoxymethylaminobenzaldehydes or N-carbalkoxyethylcarbazole-3-aldehydes aldehydes (arylidene dyes) which exhibit suitable absorption as yellow filter dyes and are completely decoloured in the layer during development.

The present invention provides a colour photographic recording material which comprises on a film support at least one red-sensitive silver halide emulsion layer with a cyan coupler, at least one green-sensitive silver halide emulsion layer with a magenta coupler, at least one blue-sensitive silver halide emulsion layer with a yellow coupler and at least one yellow coloured non-photosensitive layer which is arranged beneath a blue-sensitive silver halide emulsion layer and above a green-sensitive silver halide emulsion layer (yellow filter layer), characterised in that the material comprises in the yellow filter layer at least one dye of one of the formulae I and II.

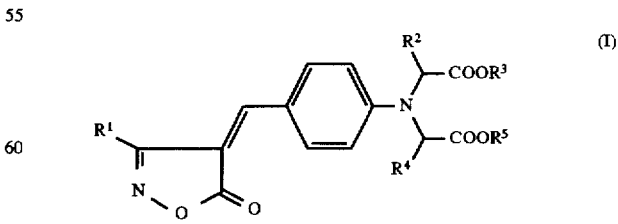

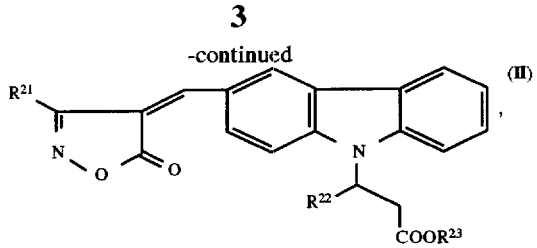

in which
R¹, R³, and R⁵ (mutually independently) mean alkyl, cycloalkyl or aryl;
R² and R⁴ (mutually independently) mean hydrogen or alkyl,
$R^{21}$ means a residue as $R^1$;
$R^{22}$ means a residue as $R^2$;
$R^{23}$ means a residue as $R^1$;
provided that in formula I none of the residues R¹ to R⁵ contains an alkyl chain of more than 3 carbon atoms.

Examples of an alkyl group represented by R¹ to R⁵ are methyl, ethyl, propyl, isopropyl, isobutyl, tert.-butyl or neopentyl. The stated alkyl groups may be unsubstituted or substituted. Examples of halogen as a substituent on one of the stated alkyl groups are fluorine, chlorine or bromine. Examples of an alkoxy group as a substituent on one of the stated alkyl groups are methoxy, ethoxy, propoxy, isopropoxy, isobutoxy, tert.-butoxy, neo-pentoxy, ethoxyethoxy or isobutoxy.

Examples of a sulfamoyl group as a substituent on one of the stated alkyl groups are N-tolylsulfamoyl or N-(1)-naphthylsulfamoyl. An example of a sulfonamido group as a substituent on one of the stated alkyl groups is tolylsulfonamido.

Examples of an aryl group as a substituent on one of the stated alkyl groups are phenyl, alkoxyphenyl, alkylsulfonamidophenyl, N-alkylsulfamoylphenyl, acylaminophenyl (alkyl groups which are substituted in this way are for example benzyl, p-propyl-sulfonamidobenzyl, p-propylsulfonamido-phenethyl or ω-(p-N-alkylsulfamoylphenyl)-propyl).

The dyes of the present invention can contain solubifying groups having a dissociable proton, such as —NH—SO₂— (sulfonamido or sulfamoyl)
—CO—NH—CO—, —CO—NH—SO₂— or —SO₂—NH—SO₂—.

None of the residues R¹ to R⁵ contains an alkyl group having more than 3 carbon atoms directly bonded together. This means that structures of the formula

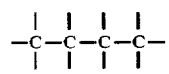

having 4 or more carbon atoms are not present in the dyes of the present invention.

Examples of dyes of formula I according to the invention are stated below:

| Dye | R¹ | R² | R³ | R⁴ | R⁵ |
|---|---|---|---|---|---|
| I-1 | —C₃H₇ | H | —C₂H₅ | H | —C₂H₅ |
| I-2 | i-C₃H₇ | H | —C₃H₇ | H | —C₃H₇ |
| I-3 | —C₃H₇ | H | —C₃H₇ | H | —C₃H₇ |
| I-4 | —C₂H₅ | —CH₃ | —C₃H₇ | H | —C₃H₇ |
| I-5 | —CH₃ | —C₂H₅ | —C₂H₅ | H | —C₂H₅ |
| I-6 | —C₃H₇ | H | —(CH₂)₂—OC₂H₅ | H | —(CH₂)₂—OC₂H₅ |
| I-7 | —C₂H₅ | H | —(CH₂)₂—OC₃H₇ | H | —(CH₂)₂—OC₃H₇ |
| I-8 | —C₃H₇ | H | —CH₂CF₃ | H | —CH₂CF₃ |
| I-9 | —C₂H₅ | H | —C₃H₇ | H | —C₃H₇ |
| I-10 | —C₃H₇ | H | —C₂H₅ | H | i-C₃H₇ |
| I-11 | —C₂H₅ | H | i-C₃H₇ | H | i-C₃H₇ |
| I-12 | —C₃H₇ | H | —(CH₂)₂—OCH₃ | H | —(CH₂)₂—OCH₃ |
| I-13 | —CH₂—OCH₃ | H | —C₃H₇ | H | —C₃H₇ |
| I-14 | —CH₂—OCH₃ | H | —(CH₂)₂—OCH₃ | H | —(CH₂)₂—OCH₃ |
| I-15 | —CH₂—OCH₃ | H | —(CH₂)₂—OC₂H₅ | H | —(CH₂)₂—OC₂H₅ |
| I-16 | —CH₂—OC₂H₅ | H | —C₃H₇ | H | —C₃H₇ |
| I-17 | —CH₂—OC₂H₅ | H | —(CH₂)₂—OCH₃ | H | —(CH₂)₂—OCH₃ |
| I-18 | —CH₂—OC₂H₅ | H | —(CH₂)₂—OC₂H₅ | H | —(CH₂)₂—OC₂H₅ |
| I-19 | —CH₂—OCH₃ | —CH₃ | —(CH₂)₂—OCH₃ | —CH₃ | —(CH₂)₂—OCH₃ |
| I-20 | cyclo-Propyl | H | —C₃H₇ | H | —C₃H₇ |
| I-21 | 4-C₆H₄—NH—SO₂C₂H₅ | H | —C₃H₇ | H | —C₃H₇ |
| I-22 | —CH₂—C₆H₄—NH—SO₂C₂H₅ | H | —C₂H₅ | H | —C₂H₅ |
| I-23 | —CH₂—C₆H₄—NH—SO₂—C₃H₇ | H | —(CH₂)—O—(CH₂)₂—O—CH₂CH(CH₃)₂ | H | same as R³ |
| I-24 | —C₃H₇ | H | —(CH₂)—O—(CH₂)₂—O—CH₂CH(CH₃)₂ | H | same as R³ |
| I-25 | —C₃H₇ | H | —CH(CH₃)—CH₂—O—C₃H₇ | H | same as R³ |
| I-26 | —C₃H₇ | H | —(CH₂)₂—O—C(CH₃)₃ | H | same as R³ |
| I-27 | —CH₂—CH(CH₃)₂ | H | —CH₂—O—CH₂CH(CH₃)₂ | H | same as R³ |
| I-28 | —CH₂—C(CH₃)₂ | H | —(CH₂)₂—O—C₃H₇ | H | same as R³ |
| I-29 | —C₃H₇ | H | —(CH₂)₂—SO₂—NH—C₆H₄—CH₃ | H | same as R³ |

-continued

| Dye | R$^1$ | R$^2$ | R$^3$ | R$^4$ | R$^5$ |
|---|---|---|---|---|---|
| I-30 | —C$_3$H$_7$ | H | —(CH$_3$)$_3$—SO$_2$—NH—(naphthyl) | H | same as R$^3$ |
| I-31 | —C$_3$H$_7$ | H | —(CH$_2$)$_2$—NH—SO$_2$—C$_6$H$_4$—CH$_3$ | H | same as R$^3$ |
| I-32 | —C$_3$H$_7$ | H | —(CH$_2$)$_3$—NH—SO$_2$—C$_6$H$_4$—CH$_3$ | H | same as R$^3$ |
| I-33 | —C$_3$H$_7$ | H | —(CH$_2$)$_2$—C$_6$H$_4$—NH—SO$_2$—C$_3$H$_7$ | H | same as R$^3$ |
| I-34 | —C$_3$H$_7$ | H | —(CH$_2$)$_3$—C$_6$H$_4$—SO$_2$—NH—(CH$_2$)$_3$—O—CH(CH$_3$)$_2$ | H | same as R$^3$ |

Examples of dyes according to the invention of the formula II are given below:

| Dye | R$^{21}$ | R$^{22}$ | R$^{23}$ |
|---|---|---|---|
| II-1 | 4-C$_6$H$_4$—NH—SO$_2$C$_2$H$_5$ | H | —C$_2$H$_5$ |
| II-2 | 4-C$_6$H$_4$—NH—SO$_2$C$_2$H$_5$ | —CH$_3$ | —C$_2$H$_5$ |
| II-3 | —C$_3$H$_7$ | H | —C$_2$H$_5$ |
| II-4 | —C$_2$H$_5$ | H | —C$_3$H$_7$ |
| II-5 | —C$_2$H$_5$ | —CH$_3$ | —C$_3$H$_7$ |
| II-6 | 4-C$_6$H$_4$—NH—SO$_2$C$_3$H$_7$ | —CH$_3$ | —C$_2$H$_5$ |
| II-7 | —CH$_2$—C$_6$H$_4$—NH—SO$_2$—CH$_3$ | H | —C$_3$H$_7$ |
| II-8 | —CH$_2$—C$_6$H$_4$—NH—SO$_2$—CH$_3$ | —CH$_3$ | —C$_3$H$_7$ |
| II-9 | —C$_3$H$_7$ | H | —(CH$_2$)—O—(CH$_2$)—O—CH$_2$—CH(CH$_3$)$_2$ |
| II-10 | —C$_3$H$_7$ | H | —(CH$_2$)$_2$O—(CH$_2$)$_2$—OC$_2$H$_5$ |
| II-11 | —(CH$_2$)$_2$—C$_6$H$_5$ | H | —(CH$_2$)$_2$—O—CH$_2$—CH(CH$_3$)$_2$ |
| II-12 | —(CH$_2$)$_3$—C$_6$H$_5$ | H | —(CH$_2$)$_2$—O—C$_2$H$_5$ |

The dyes used according to the invention may readily be produced by condensing an isoxazolone with a suitable aldehyde. It may also be possible to dispense with isolation of the isoxazolone, as is shown in the following example.
Production of Dye 3

63.2 g of butyryl acetic ester are refluxed for 30 minutes with 27.8 g of hydroxylammonium chloride in 400 ml of ethanol with the addition of 40.4 g of triethylamine. 128.4 g of 4-N-bispropoxycarbonylmethylaminobenzaldehyde are then added and the mixture refluxed for a further hour. 200 ml of water are added to the hot condensation solution and the dye crystallises out on cooling. The dye is suction filtered and dried. 113 g of dye of a melting point of 85° to 87° C. are obtained having an absorption maximum of 446 nm (in methanol).

The dyes according to the invention are used in hydrophilic binders, preferably in gelatine. The dyes may be introduced into a gelatine layer in various manners. The method of introduction strongly influences the shape of the absorption curve and dye absorption may be adjusted to the intended application in this manner.

The dyes according to the invention may readily be introduced into the casting solution by using high boiling solvents, so-called oil formers. Corresponding methods are described, for example, in U.S. Pat. No. 2,322,027, U.S. Pat. No. 2,801,170, U.S. Pat. No. 2,801,171 and EP-A-0 043 037. Oligomers or polymers, so-called polymeric oil formers, may be used instead of high-boiling solvents.

Suitable oil formers are, for example, phthalic acid esters, phosphoric acid esters, phosphonic acid esters, citric acid esters, benzoic acid esters, amides, fatty acid esters, alcohols, phenols, aniline derivatives, alkylpyrrolidones and hydrocarbons.

The dyes according to the invention may also be used in the form of dispersions of fine solid particles. Such dispersions are obtained by precipitation reactions or by grinding the dyes in sand or colloid mills. The dispersions should preferably have an average particle size of less than 1 μm, preferably less than 0.5 μm.

The dyes may be used alone or in combination with other filter dyes, masking dyes, UV absorbers, silver filter yellow etc. To this end, they are usually incorporated into separate layers, but the dyes may also be added directly to the emulsion layers. The quantity used may be between 1 and 1000 mg/m$^2$, preferably 10 to 200 mg/m$^2$.

According to a preferred embodiment of the present invention, the dyes of the formula I are used in a yellow filter layer which is preferably arranged between a blue-sensitive layer and the underlying green-sensitive and red-sensitive layers of a photographic recording material.

The dyes used according to the invention have excellent non-diffusibility and may still be rapidly and completely removed from the photographic material when treated with solutions as are conventional in photographic processing.

The present invention is suitable for photographic materials containing any silver halide emulsions. These emulsions may contain silver bromide, silver chloride or mixtures thereof, possibly having a low silver iodide content of up to 10 mol. %, as the silver halide.

Examples of colour photographic materials are colour negative films, colour reversal films, colour positive films, colour photographic paper, colour reversal photographic paper, colour-sensitive materials for the dye diffusion transfer process or the silver dye bleaching process.

The photographic materials consist of a support onto which at least one photosensitive silver halide emulsion layer is applied. Thin films and sheets are in particular suitable as supports. A review of support materials and the auxiliary layers applied to the front and reverse sides of which is given in Research Disclosure 37254, part 1 (1995), page 285.

The colour photographic materials conventionally contain at least one red-senstive, one green-sensitive and one blue-sensitive silver halide emulsion layer, optionally together with interlayers and protective layers.

Depending upon the type of the photographic material, these layers may be differently arranged. This is demonstrated for the most important products:

Colour photographic films such as colour negative films and colour reversal films have on the support, in the stated sequence, 2 or 3 red-sensitive, cyan-coupling silver halide emulsion layers, 2 or 3 green-sensitive, magenta-coupling silver halide emulsion layers and 2 or 3 blue-sensitive, yellow-coupling silver halide emulsion layers. The layers of identical spectral sensitivity differ with regard to their photographic sensitivity, wherein the less sensitive partial layers are generally arranged closer to the support than the more highly sensitive partial layers.

The number and arrangement of the photosensitive layers may be varied in order to achieve specific results. For example, all high sensitivity layers may be grouped together in one package of layers and all low sensitivity layers may be grouped together another package of layers in order to increase sensitivity (DE 2 530 645).

The substantial constituents of the photographic emulsion layers are binder, silver halide grains and colour couplers.

Details of suitable binders may be found in Research Disclosure 37254, part 2 (1995), page 286.

Details of suitable silver halide emulsions, the production, ripening, stabilisation and spectral sensitisation thereof, including suitable spectral sensitisers, may be found in Research Disclosure 37254, part 3 (1995), page 286 and in Research Disclosure 37038, part XV (1995), page 89.

Photographic materials with camera sensitivity conventionally contain silver bromide-iodide emulsions, which may optionally also contain small proportions of silver chloride. Photographic print materials contain either silver chloride-bromide emulsions with up to 80 wt. % of AgBr or silver chloride-bromide emulsions with above 95 mol. % of AgCl.

Details relating to colour couplers may be found in Research Disclosure 37254, part 4 (1995), page 288 and in Research Disclosure 37038, part II (1995), page 80. The maximum absorption of the dyes formed from the couplers and the developer oxidation product is preferably within the following ranges: yellow coupler 430 to 460 nm, magenta coupler 540 to 560 nm, cyan coupler 630 to 700 nm.

In order to improve sensitivity, grain, sharpness and colour separation in colour photographic films, compounds are frequently used which, on reaction with the developer oxidation product, release photographically active compounds, for example DIR couplers which eliminate a development inhibitor.

Details relating to such compounds, in particular couplers, may be found in Research Disclosure 37254, part 5 (1995), page 290 and in Research Disclosure 37038, part XIV (1995), page 86.

Colour couplers, which are usually hydrophobic, as well as other hydrophobic constituents of the layers, are conventionally dissolved or dispersed in high-boiling organic solvents. These solutions or dispersions are then emulsified into an aqueous binder solution (conventionally a gelatine solution) and, once the layers have dried, are present as fine droplets (0.05 to 0.8 µm in diameter) in the layers.

Suitable high-boiling organic solvents, methods for the introduction thereof into the layers of a photographic material and further methods for introducing chemical compounds into photographic layers may be found in Research Disclosure 37254, part 6 (1995), page 292.

The non-photosensitive interlayers generally located between layers of different spectral sensitivity may contain agents which prevent an undesirable diffusion of developer oxidation products from one photosensitive layer into another photo-sensitive layer with a different spectral sensitisation.

Suitable compounds (white couplers, scavengers or DOP scavengers) may be found in Research Disclosure 37254, part 7 (1995), page 292 and in Research Disclosure 37038, part III (1995), page 84.

The photographic material may also contain UV light absorbing compounds, optical whiteners, spacers, filter dyes, formalin scavengers, light stabilisers, anti-oxidants, $D_{min}$ dyes, additives to improve stabilisation of dyes, couplers and whites and to reduce colour fogging, plasticisers (latices), biocides and others.

Suitable compounds may be found in Research Disclosure 37254, part 8 (1995), page 292 and in Research Disclosure 37038, parts IV, V, VI, VII, X, XI and XIII (1995), pages 84 et seq.

The layers of colour photographic materials are conventionally hardened, i.e. the binder used, preferably gelatine, is crosslinked by appropriate chemical methods.

Suitable hardener substances may be found in Research Disclosure 37254, part 9 (1995), page 294 and in Research Disclosure 37038, part XII (1995), page 86.

Once exposed with an image, colour photographic materials are processed using different processes depending upon their nature. Details relating to processing methods and the necessary chemicals are disclosed in Research Disclosure 37254, part 10 (1995), page 294 and in Research Disclosure 37038, parts XVI to XXIII (1995), pages 95 et seq. together with example materials.

EXAMPLE 1

The following layers were applied onto a cellulose acetate support provided with a coupling layer (quantities stated in g/m²)

Layer 1

| Dye I-3 | 0.2 |
|---|---|
| Gelatine | 1.0 |

Layer 2 (hardening layer)

| | |
|---|---|
| Hardener XH-1 | 0.32 |
| Gelatine | 0.5 |

Production of Dye Emulsion 0.8 g of dye I-3 are dissolved together with 0.8 g of diethyllauramide in 3 ml of ethyl acetate and dispersed with vigorous stirring in 80 ml of a 5% gelatine solution.

A clear dye layer is obtained in which the dye is present as a monomolecular solution. Dye absorption is shown in FIG. 1.

In order to assess the decolorability of the dye in the gelatine layers on development, the layer was treated using a colour negative process described in *British Journal of Photography*, 1974, pages 597 and 598 and developed using the colour reversal process as described in *Manual of Processing Kodak Ektachrome Film Using Process 7* (cf Kodak publication no. 7-119).

In both cases, the layers were completely decoloured.

EXAMPLE 2 a.) 3.0 g of dye I-1 are ground for 14 hours together with 80 ml of a 2% aqueous gelatine solution and 1.5 g of the wetting agent Baykanol SL® (Bayer) in a mill with 300 g of zirconium oxide beads of a diameter of 0.8 to 1.0 mm. The zirconium oxide beads are removed by suction filtration and washed with 159 ml of water, the dye dispersion is stirred into 52 g of 20% aqueous gelatine and made up to 300 g with water. The average particle size of the dye dispersion is 440 nm. The dye dispersion is applied at a rate of 200 mg of dye/m$^2$ onto a cellulose acetate support and overcoated with a hardening layer.

Figure 2:
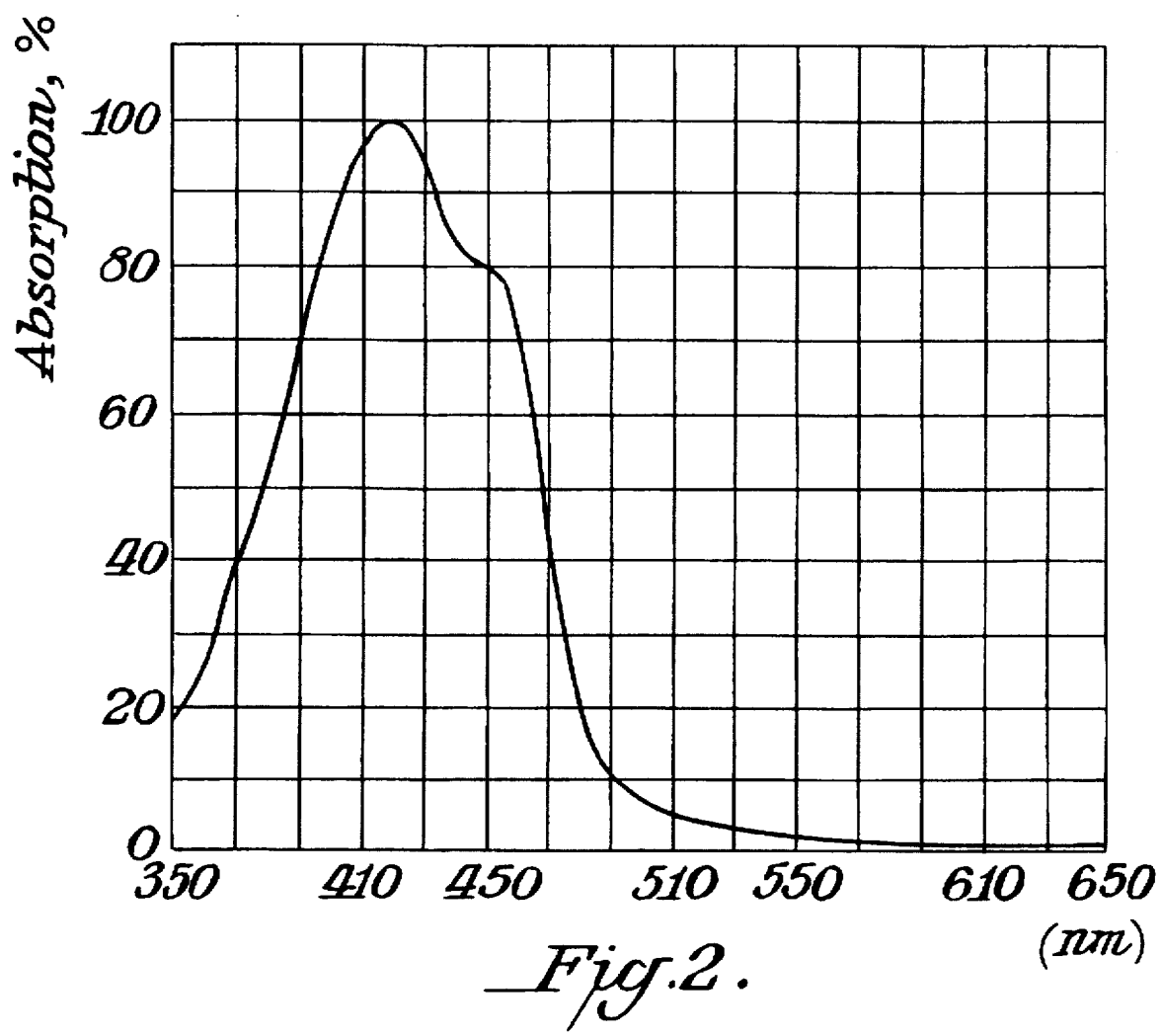

Dye layer absorption is shown in FIG. 2. In comparison with the absorption curve in FIG. 1, it may clearly be seen that the absorption maximum of the dispersion has been shifted towards a shorter wavelength (from 437 nm to 422 nm) and that an additional absorption band shifted towards a longer wavelength (at 455 nm) is formed. This increases the half-intensity width from 69 to 90 nm.

When processed using the colour negative process, the dye layer containing the dispersed dye was completely decoloured.

b.) 6.0 g of dye I-32 are ground for 7 hours together with 75 ml of a 2% aqueous gelatine solution and 1.5 g of Baykanol SL® in a mill with 300 g of zirconium oxide beads. The zirconium oxide beads are removed by suction filtration and washed with 400 ml of water, the dye dispersion is stirred into 113 g of 20% aqueous gelatine and made up to 600 ml with water. The average particle size of the dye dispersion is 210 nm. The dye dispersion is applied at a rate of 355 mg of dye/m$^2$ onto a cellulose acetate support and overcoated with a hardening layer.

The absorption maximum of the dye layer is at 440 nm. The absorption spectrum also has a shoulder at 456 nm. By processing in the usual colour negative process the dye layer containing the dispersed dye is completely decoloured.

EXAMPLE 3

A colour photographic recording material for colour negative development was produced (sample 3.1), by applying the following layers in the stated sequence onto a 120 μm thick, transparent cellulose triacetate film support provided with a coupling layer. Quantities are stated in g/m$^2$. The applied quantity of silver halide is stated as the corresponding quantities of AgNO$_3$. All the silver halide emulsions were stabilised with 0.1 g of 4-hydroxy-6-methyl-1,3,3a,7-tetraazaindene per 100 g of AgNO$_3$. The silver halide emulsions are characterised by the composition of the halide, and, with regard to grain size, by the median particle size by volume (VSP or $\bar{d}_v$). The median particle size by volume has the dimension of a length [μm] and is determined using the equation $$VSP = \bar{d}_v = \frac{\Sigma n_i d_i^4}{\Sigma n_i d_i^3}$$

wherein $n_i$ means the number of particles in the range i and $d_i$ means the diameter of spheres of an identical volume for the particles in the range i.

Sample 3.1

Layer 1: (Anti-halo layer)

| | |
|---|---|
| Dye XF-1 | 0.12 |
| Dye XF-2 | 0.12 |
| Gelatine | 0.8 |

Layer 2: (Low sensitivity, red-sensitised layer)

| | |
|---|---|
| Red-sensitised silver bromide-iodide-chloride emulsion (2.4 mol. % iodide; 10.5 mol. % chloride; VSP 0.35) | 0.85 |
| Gelatine | 0.6 |
| Cyan coupler XC-1 | 0.3 |
| Coloured coupler XCR-1 | $2.0 \times 10^{-2}$ |
| Coloured coupler XCY-1 | $1.0 \times 10^{-2}$ |
| DIR coupler XDIR-1 | $1.0 \times 10^{-2}$ |

Layer 3: (Medium sensitivity, red-sensitised layer)

| | |
|---|---|
| Red-sensitised silver bromide-iodide emulsion (10.0 mol. % iodide, VSP 0.56) | 1.2 |
| Gelatine | 0.9 |
| Cyan coupler XC-1 | 0.2 |
| Coloured coupler XCR-1 | $7.0 \times 10^{-2}$ |
| Coloured coupler XCY-1 | $3.0 \times 10^{-2}$ |
| DIR coupler XDIR-1 | $4.0 \times 10^{-3}$ |

Layer 4: (High sensitivity, red-sensitised layer)
Red-sensitised silver bromide-iodide emulsion
(6.8 mol. % iodide; VSP 1.2) 1.6

| | |
|---|---|
| Gelatine | 1.2 |
| Cyan coupler XC-2 | 0.15 |
| DIR coupler XDIR-3 | $3.0 \times 10^{-2}$ |

Layer 5: (Interlayer)

| | |
|---|---|
| Dye XF-3 | 0.12 |
| Gelatine | 1.0 |

Layer 6: (Low-sensitivity, green-sensitised layer)

| | |
|---|---|
| Green-sensitised silver bromide-iodide-chloride emulsion (9.5 mol. % iodide; 10.4 mol. % chloride; VSP 0.5) | 0.85 |
| Gelatine | 0.9 |
| Magenta coupler XM-1 | 0.3 |
| Coloured coupler XMY-1 | $2.0 \times 10^{-2}$ |
| DIR coupler XDIR-1 | $5.0 \times 10^{-3}$ |
| DIR coupler XDIR-2 | $1.0 \times 10^{-3}$ |
| Oxform scavenger XSC-1 | $5.0 \times 10^{-2}$ |

Layer 7: (Medium-sensitivity, green-sensitised layer)

| | |
|---|---|
| Green-sensitised silver bromide-iodide emulsion (10.0 mol. % iodide; VSP 0.56) | 1.4 |
| Gelatine | 0.9 |
| Magenta coupler XM-1 | 0.24 |
| Coloured coupler XMY-1 | $4.0 \times 10^{-2}$ |
| DIR coupler XDIR-1 | $5.0 \times 10^{-3}$ |
| DIR coupler XDIR-2 | $3.0 \times 10^{-3}$ |

Layer 8: (High-sensitivity, green-sensitised layer)

| | |
|---|---|
| Green-sensitised silver bromide-iodide emulsion (6.8 mol. % iodide; VSP 1.1) | 1.7 |
| Gelatine | 1.2 |
| Magenta coupler XM-2 | $3.0 \times 10^{-2}$ |
| Coloured coupler XMY-2 | $5.0 \times 10^{-2}$ |
| DIR coupler XDIR-3 | $5.0 \times 10^{-2}$ |

Layer 9: (Interlayer)

| | |
|---|---|
| Gelatine | 0.4 |
| Polyvinylpyrrolidone | $1.0 \times 10^{-2}$ |

Layer 10: (Yellow filter layer)

| | |
|---|---|
| Yellow coloidal silver sol (silver filter yellow), Ag | 0.1 |
| Gelatine | 0.8 |
| Polyvinylpyrrolidone | 0.2 |
| Oxform scavenger XSC-2 | $6.0 \times 10^{-2}$ |

Layer 11: (Low-sensitivity blue-sensitised layer)

| | |
|---|---|
| Blue-sensitised silver bromide-iodide-chloride emulsion (6.0 mol. % iodide; VSP 0.78) | 0.4 |
| Gelatine | 1.0 |
| Yellow coupler XY-1 | 0.4 |
| DIR coupler XDIR-1 | $3.0 \times 10^{-2}$ |

Layer 12: (Medium-sensitivity, blue-sensitised layer)

| | |
|---|---|
| Blue-sensitised silver bromide-iodide emulsion (8.8 mol. % iodide; 15.0 mol. % chloride; VSP 0.77) | 0.12 |
| (12.0 mol. % iodide; 15.0 mol. % chloride; VSP 1.0) | 0.28 |
| Gelatine | 0.77 |
| Yellow coupler XY-1 | 0.58 |

Layer 13: (High-sensitivity, blue-sensitised layer)

| | |
|---|---|
| Blue-sensitised silver bromide-iodide emulsion (12.0 mol. % iodide; VSP 1.2) | 1.2 |
| Gelatine | 0.9 |
| Yellow coupler XY-1 | 0.1 |
| DIR coupler XDIR-3 | $2.0 \times 10^{-2}$ |

Layer 14: (Protective layer)

| | |
|---|---|
| Micrate silver bromide-iodide emulsion (4.0 mol. % iodide; VSP 0.05) | 0.25 |
| UV absorber XUV-1 | 0.2 |
| UV absorber XUV-2 | 0.3 |
| Gelatine | 1.4 |

Layer 15: (Hardening layer)

| | |
|---|---|
| Gelatine | 0.2 |
| Hardener XH-1 | 0.86 |
| Persoftal | 0.04 |

Compounds used in Example 3:

XF-1

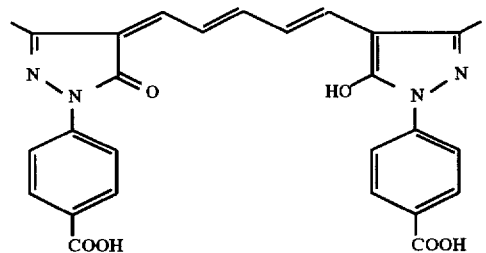

XF-2

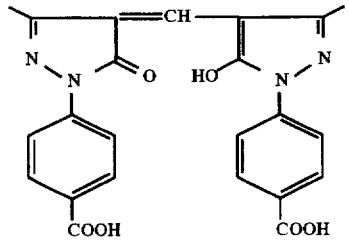

-continued
XF-3
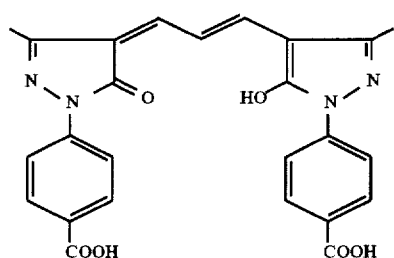
XC-1
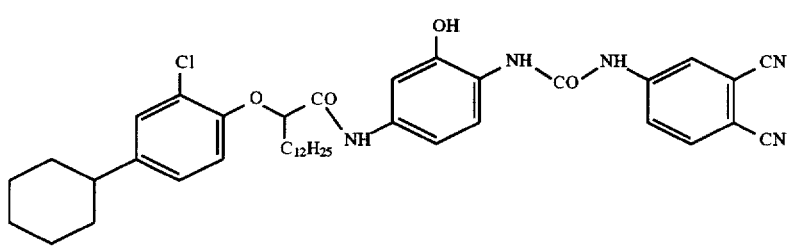
XC-2
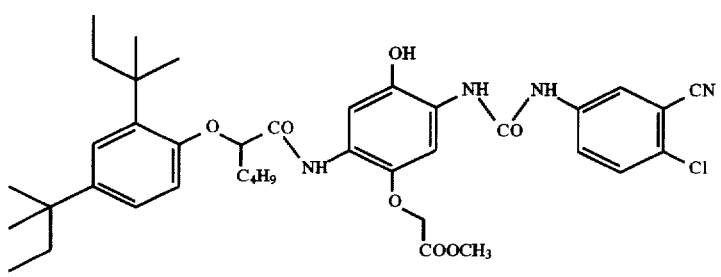
XCR-1
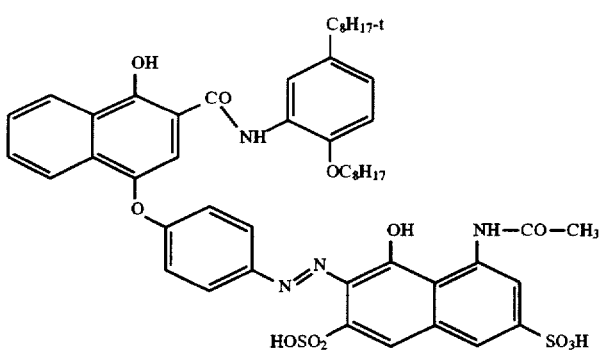

XCY-1
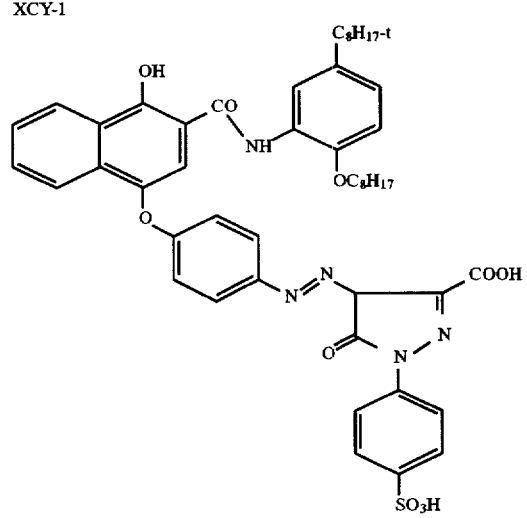
-continued
XCY-1
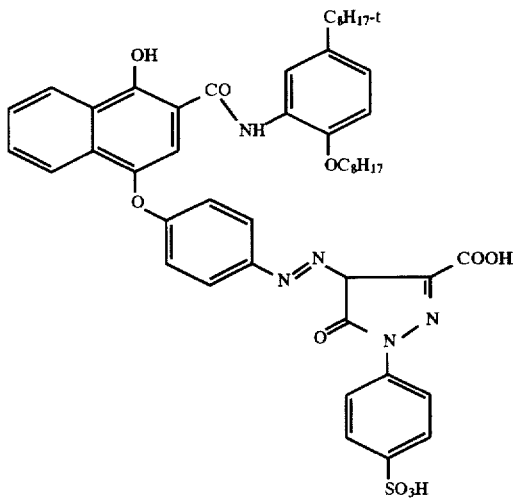
XM-1
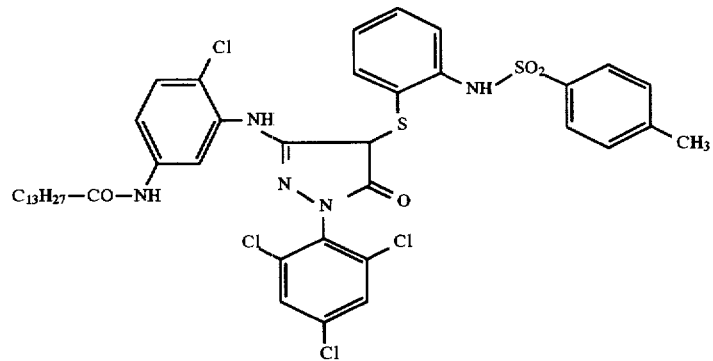
XM-2
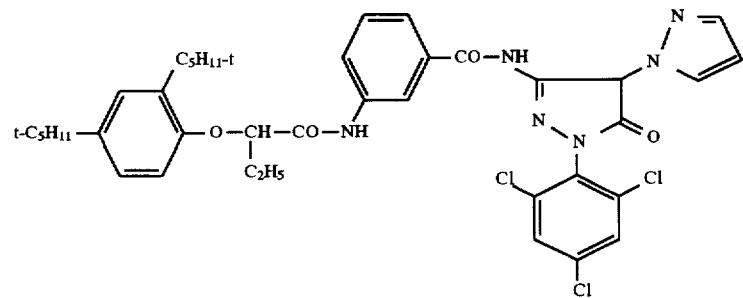
XMY-1
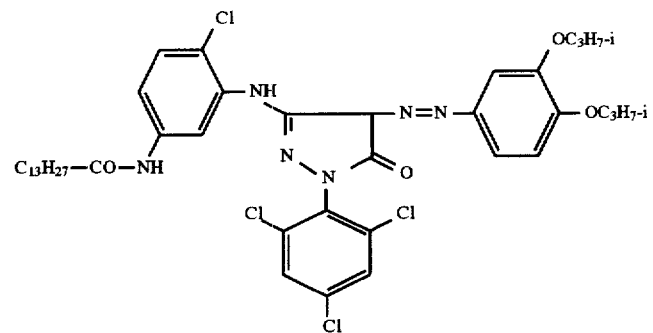

-continued
XMY-2
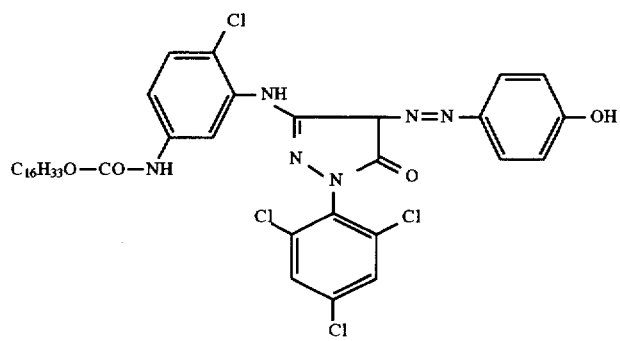
XY-1
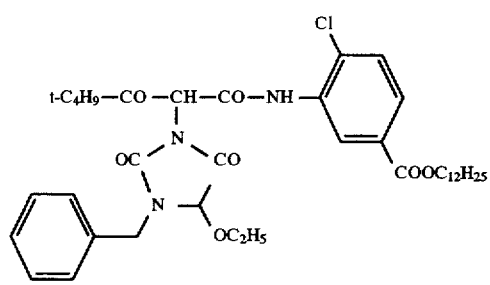
XDIR-1
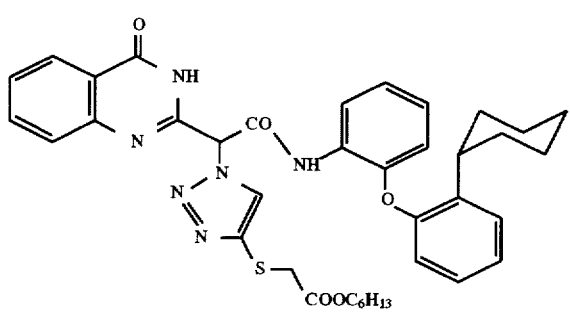
XDIR-2
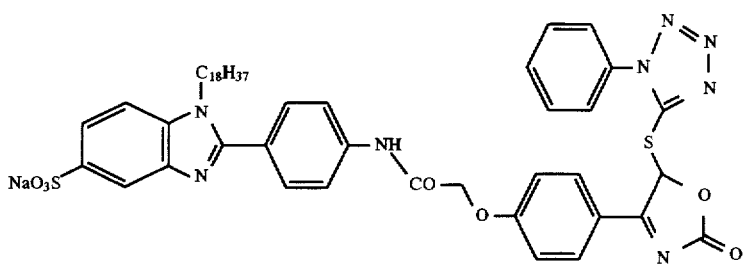
XDIR-3
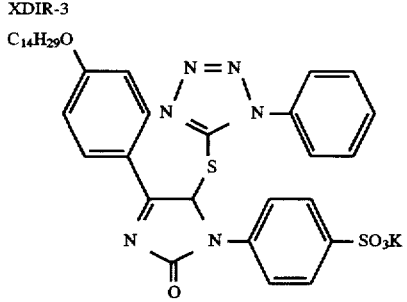
XSC-1
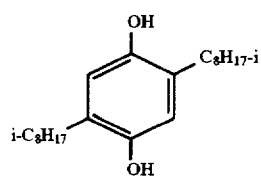
XSC-2
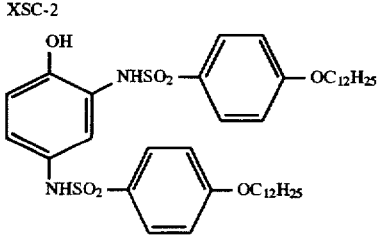

XUV-1

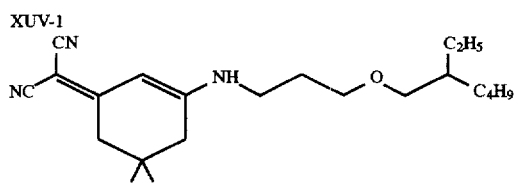

R¹ = —C₈H₁₇
R² = —CH₂—CH—C₄H₉
         |
         C₂H₅
R¹/R² = 1:1

-continued
XUV-2

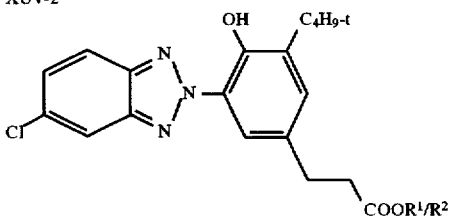

XH-1

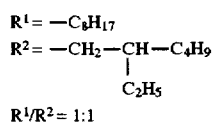

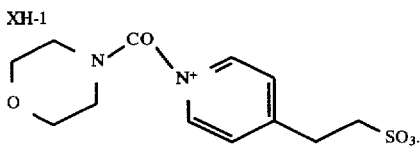

The colourless and coloured couplers were each incorporated together with the same quantity of tricresyl phosphate (TCP) using known emulsion methods.

General emulsification method for the dyes according to the invention in Example 3:

10 g of the dye according to the invention are dissolved together with 20 g of TCP and 40 g of ethyl acetate and emulsified with a high speed mixer at 50° C. into 200 g of 10% gelatine, which had been combined with 0.05 g of Erkantol. The ethyl acetate was then stripped out under a vacuum. The still liquid dispersion was then solidified at 6° C.

Samples 3.2 to 3.11

The samples differ from sample 3.1 in that they contain a filter dye according to the invention in layer 10 instead of Carey Lea silver (silver filter yellow). The various materials were then exposed with daylight through a graduated grey wedge and through a Status M blue filter. The materials were then processed as described in Example 1 using the process described in E. Ch. Gehret, *The British Journal of Photography* 1974, p. 597. Relative green sensitivity and blue/green colour separation may be measured on the resultant samples.

The results indicate that the dyes according to the invention allow either higher sensitivity or, at constant sensitivity, better colour separation, which results in improved colour reproduction in the developed image in comparison with a conventional Carey Lea filter.

Table I below shows the corresponding combinations and the results obtained therewith.

TABLE 1

| Sample | Dye | Quantity | Rel. green sensitivity | Blue/green colour separation Δ log H | |
|---|---|---|---|---|---|
| 3.1 | Carey Lea Ag | 0.040 g | 100 | 1.03 | Comparison |
| 3.2 | I-1 | 0.065 g | 129 | 1.05 | Invention |
| 3.3 | I-3 | 0.070 g | 125 | 1.06 | Invention |
| 3.4 | I-3 | 0.140 g | 112 | 1.32 | Invention |
| 3.5 | I-3 | 0.200 g | 100 | 1.52 | Invention |
| 3.6 | I-4 | 0.070 g | 125 | 1.05 | Invention |
| 3.7 | I-11 | 0.068 g | 125 | 1.05 | Invention |
| 3.8 | 1-16 | 0.072 g | 123 | 1.04 | Invention |
| 3.9 | 1-25 | 0.255 g | 100 | 1.51 | Invention |
| 3.10 | II-9 | 0.280 g | 100 | 1.33 | Invention |
| 3.11 | I-10 | 0.265 g | 100 | 1.31 | Invention |

EXAMPLE 4

Sample 4.1 differs from sample 3.1 in that layer 10 contained no Carey Lea silver, but in addition contained 100 mg of a polyurethane synthesised from an addition product of a polyester diol with hexamethylene diisocyanate and aminoethanesulphonic acid. Samples 4.2 to 4.10 additionally contained the filter dye shown in Table 2. The corresponding materials were then processed as described in Example 3. Relative blue and green sensitivity and the difference in yellow coloration in the fog range of samples 4.2 to 4.10 were then measured in comparison with sample 4.1.

TABLE 2

| Sample | Compound | Quantity | Rel. blue sensitivity | Rel. green sensitivity | Δ yellow coloration relative to sample 4.1 | |
|---|---|---|---|---|---|---|
| 4.1 | None | 0 | 100 | not measured | | Rel. comparison |
| 4.2 | Dye A | 0.150 g | 100 | 100 | 0.015 | Comparison |
| 4.3 | Dye B | 0.144 g | 109 | 90 | 0.4 | Comparison |
| 4.4 | Dye C | 0.132 g | 107 | 107 | 0.060 | Comparison |
| 4.5 | Compound I-2 | 0.105 g | 107 | 125 | 0.010 | Invention |
| 4.6 | Compound I-3 | 0.105 g | 107 | 125 | 0.010 | Invention |
| 4.7 | Compound I-5 | 0.080 g | 105 | 129 | 0 | Invention |
| 4.8 | Compound I-23 | 0.111 g | 107 | 129 | 0.010 | Invention |

TABLE 2-continued

| Sample | Compound | Quantity | Rel. blue sensitivity | Rel. green sensitivity | Δ yellow coloration relative to sample 4.1 | |
|---|---|---|---|---|---|---|
| 4.9 | Compound I-32* | 0.130 g | 105 | 122 | 0.010 | Invention |
| 4.10 | Compound I-9 | 0.148 g | 105 | 114 | 0.010 | Invention |

*Dispersion of solid particles obtained from Example 2b.

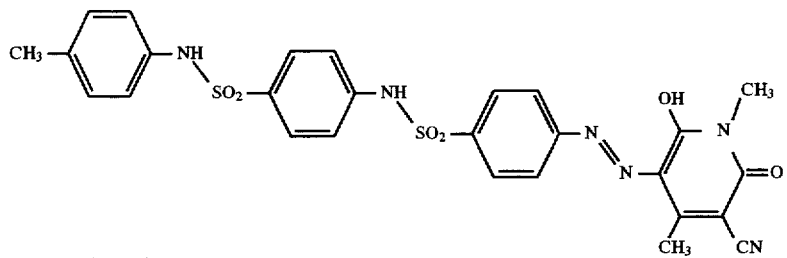

Dye A (= dye 28 from DE-A-4 428 292)

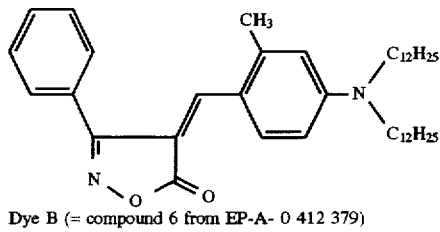

Dye B (= compound 6 from EP-A- 0 412 379)

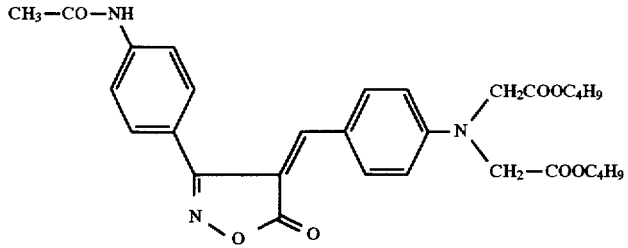

Dye C (= compound 31 from EP-A-0 412 379)

It is clear from the results in Table 2 that, in a complete film material, the compounds according to the invention bring about distinctly less coloration and greater green sensitivity than the comparison compounds. The very similar comparison compounds in samples 4.3 and 4.4 bring about lower green sensitivity as they absorb to some extent in the green range of the spectrum.

EXAMPLE 5

The same method was used as in sample 3.1, with the difference that 0.24 g of magenta coupler XM-3 were introduced into layer 6 and 0.17 g of magenta coupler XM-3 were introduced into layer 7 instead of magenta coupler XM-1 (sample 5.1). 0.6 g of compound XFF-1 were furthermore additionally introduced into the layer structure above layer 10. Instead of Carey Lea silver, the filter dye used was 0.075 g of filter dye D, which is identical to Y 32 from U.S. Pat. No. 4,764,455. Table 3 shows the filter dyes used in layer 10 in samples 5.2 to 5.9 together with the results. A proportion of the materials was stored under normal room conditions and another proportion was also stored for 7 days at 35°/90% relative humidity. The material was then developed as described in Example 3 and the difference in green sensitivity (ΔE green) and difference in fog (ΔS magenta) between normal storage and storage at 35°/90% relative humidity were determined.

TABLE 3

| Sample | Compound | Quantity | ΔE green log H | ΔS magenta | |
|---|---|---|---|---|---|
| 5.1 | D | 0.075 | −0.40 | 0.45 | Comparison |
| 5.2 | E | 0.090 | −0.12 | 0.02 | Comparison |
| 5.3 | F | 0.060 | −0.10 | 0.12 | Comparison |
| 5.4 | Compound I-3 | 0.070 | −0.04 | 0.02 | Invention |
| 5.5 | Compound I-4 | 0.070 | −0.03 | 0.01 | Invention |
| 5.6 | Compound I-12 | 0.074 | −0.02 | 0.02 | Invention |
| 5.7 | Compound I-17 | 0.077 | −0.04 | 0.03 | Invention |
| 5.8 | Compound I-32* | 0.125 | −0.03 | 0.02 | Invention |
| 5.9 | Compound II-9 | 0.100 | −0.04 | 0.02 | Invention |

*Dispersion of solid particles obtained from Example 2b.

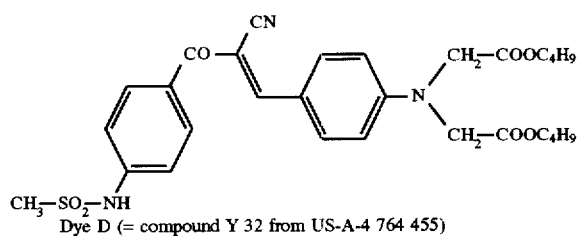

Dye D (= compound Y 32 from US-A-4 764 455)

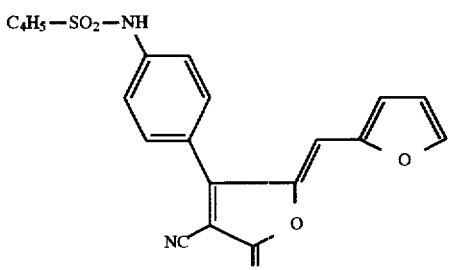

Dye E (= compound 1 from US-A-4 923 788)

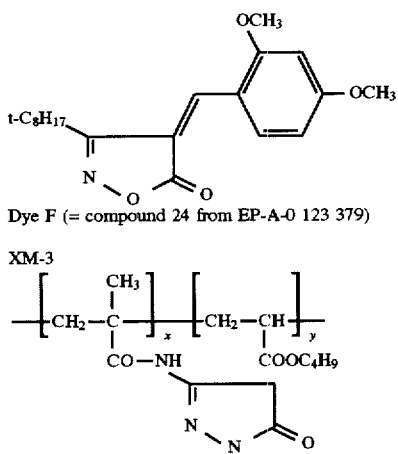

Dye F (= compound 24 from EP-A-0 123 379)

XM-3

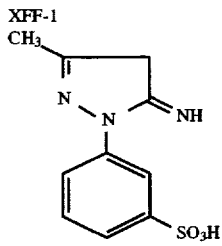

x,y = 50 wt %

XFF-1

It may be seen from Table 3 that the examples according to the invention exhibit advantages both with regard to a lower reduction in sensitivity and with regard to fogging under tropical conditions.

EXAMPLE 6

The same method was used as in Example 1, with the difference that the oil formers were varied for various dyes according to the invention. Two parts by weight of oil former were used for each part by weight of dye. The absorption maxima and half-intensity widths were then determined. Table 3 shows the variants and results.

TABLE 4

| Sample | Compound | Oil former | Absorption maximum [nm] | Half-intensity width [nm] |
|---|---|---|---|---|
| 6.1 | I-3 | Diethyllauramide | 440 | 76 |
| 6.2 | I-3 | TCP | 445 | 80 |
| 6.3 | I-3 | N-Octylpyrrolidone | 438 | 72 |
| 6.4 | I-4 | TCP | 441 | 80 |
| 6.5 | I-4 | N-Octylpyrrolidone | 438 | 73 |
| 6.6 | I-4 | Cyclohexylpyrrolidone | 438 | 73 |
| 6.7 | II-6 | TCP | 446 | 81 |
| 6.8 | II-6 | iso-Octylpyrrolidone | 440 | 73 |
| 6.9 | II-6 | Nonylpyrrolidone | 440 | 73 |

It may be seen from Table 4 that incorporation with alkylpyrrolidone in particular results in sharp and narrow-banded absorption, which is also particularly favourable for photographic materials.

We claim:

1. Color photographic recording material which comprises on a film support at least one red-sensitive silver halide emulsion layer with a cyan coupler, at least one green-sensitive silver halide emulsion layer with a magenta coupler, at least one blue-sensitive silver halide emulsion layer with a yellow coupler and at least one yellow coloured non-photosensitive layer which is arranged beneath a blue-sensitive silver halide emulsion layer and above a green-sensitive silver halide emulsion layer (yellow filler layer), wherein the material comprises in the yellow filter layer at least one dye of one of the formulae I and II.

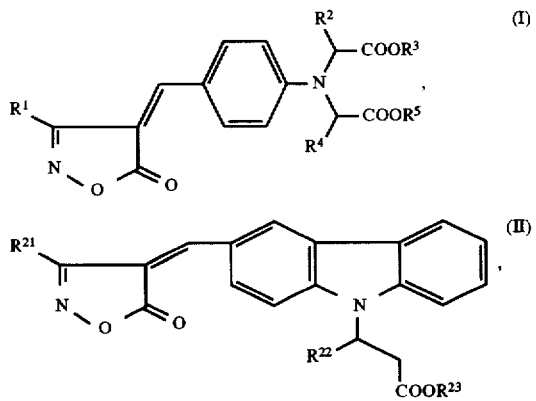

in which

R$^1$, R$^3$, and R$^5$ (mutually independently) mean alkyl or cycloalkyl;

R$^2$ and R$^4$ (mutually independently) mean hydrogen or alkyl;

R$^{21}$ means a residue as R$^1$;

R$^{22}$ means a residue as R$^2$;

R$^{23}$ means a residue as R$^1$, provided that in formula I none of the residues R$^1$ to R$^5$ contains an alkyl chain of more than 3 carbon atoms.

2. Recording material according to claim 1, wherein the dye of the formula I or II is present in the yellow filter layer in the form of a solution in an oil former.

3. Recording material according to claim 1, wherein the dye of the formula I or II is present in the yellow filter layer in the form of a dispersion of fine solid particles.

4. Recording material according to claim 2, wherein the yellow filter layer comprises an alkylpyrrolidone as the oil former.

5. Recording material according to claim 1, wherein the yellow filter layer comprises polyvinylpyrrolidone.

6. The recording material according to claim 1, wherein $R^1$ is —$C_3H_7$, —$C_2H_6$ or —$CH_3$.

7. The recording material according to claim 1, wherein $R^2$ is H, —$CH_3$ or —$C_2H_5$.

8. The recording material according to claim 3, wherein $R^2$ is H.

9. The recording material according to claim 8, wherein $R^1$ is —$C_3H_7$.

10. The recording material according to claim 1, wherein $R^4$ is H or —$CH_3$.

11. The recording material according to claim 9, wherein $R^4$ is H.

12. The recording material according to claim 1, wherein $R^5$ is —$C_2H_5$,—$C_3H_7$ —$(CH_2)_2$—$OC_2H_5$,—$(CH_2)_2OC_3H_7$ or —$CH_2CF_3$.

13. The recording material according to claim 11, wherein $R^5$ is —$C_3H_7$.

14. The recording material according to claim 1, wherein $R^3$ is —$C_2H_5$, —$C_3H_7$, —$(CH_2)_2$—$OC_2H_5$, —$(CH_2)_2$—$OC_3H_7$(CH_2)_2$—$OCH_3$ or —$CH_2CF_3$.

15. The recording material according to claim 13, wherein $R^3$ is —$C_3H_7$.

16. The recording material according to claim 1, wherein at least one dye of formula II is present and $R^{21}$ is —$C_3H_7$ or —$C_2H_5$.

17. The recording material according to claim 1 wherein at least one dye of formula II is present and $R^{22}$ is H or —$CH_3$.

18. The recording material according to claim 1, wherein formula II is present and $R^{23}$ is —$C_2H_5$, —$C_3H_7$,—$(CH_2)$—$O$—$(CH_2)$—$O$—$CH_2$—$CH(CH_3)_2$ or —$(CH_2)_2$—$O$—$(CH_2)_2$—$OC_2H_5$.

19. The recording material according to claim 16, wherein $R^{23}$ is —$C_2H_5$ or —$C_3H_7$.

20. Color photographic recording material which comprises on a film support at least one red-sensitive silver halide emulsion layer with a cyan coupler, at least one green-sensitive silver halide emulsion layer with a magenta coupler, at least one blue-sensitive silver halide emulsion layer with a yellow coupler and at least one yellow coloured non-photosensitive layer which is arranged beneath a blue-sensitive silver halide emulsion layer and above a green-sensitive silver halide emulsion layer (yellow filter layer), wherein the material comprises in the yellow filter layer at least one dye of one of the formulae I and II,

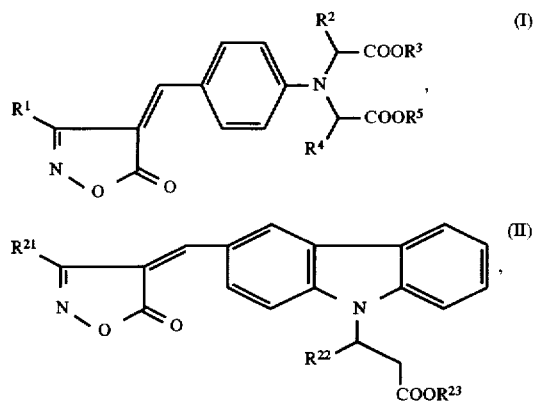

in which $R^1$ is alkyl or cycloalkyl;

$R^3$ and $R^5$ (mutually independently) are alkyl, cycloalkyl or aryl;

$R^2$ and $R^4$ (mutually independently) mean hydrogen or alkyl;

$R^{21}$ means alkyl, cycloalkyl or aryl;

$R^{22}$ means a residue an $R^2$;

$R^{23}$ means alkyl, cycloalkyl or aryl;

provided that in formula I none or the residues $R^1$ to $R^5$ contains an alkyl chain of more than 3 carbon atoms.

* * * * *

UNITED STATES PATENT AND TRADEMARK OFFICE
CERTIFICATE OF CORRECTION

PATENT NO. : 5,776,667
DATED : July 7, 1998
INVENTOR(S) : HANS ÖHLSCHLÄGER ET AL.

It is certified that error appears in the above-identified patent and that said Letters Patent is hereby corrected as shown below:

In claim 6, line 2, at column 25, please delete "$C_2H_6$" and insert -- $C_2H_5$ -- thereof.

In claim 20, column 26, second to the last line, after the phrase "provided that in formula I none", please delete the word "or" and insert the word -- of -- thereof.

Signed and Sealed this

Twentieth Day of October, 1998

Attest:

BRUCE LEHMAN

*Attesting Officer*  *Commissioner of Patents and Trademarks*